United States Patent
Najafi et al.

(10) Patent No.: US 7,211,048 B1
(45) Date of Patent: May 1, 2007

(54) SYSTEM FOR MONITORING CONDUIT OBSTRUCTION

(75) Inventors: Nader Najafi, Ann Arbor, MI (US); Collin Anderson Rich, Ypsilanti, MI (US); Sonbol Massoud-Ansari, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 480 days.

(21) Appl. No.: 10/679,916

(22) Filed: Oct. 6, 2003

Related U.S. Application Data

(60) Provisional application No. 60/416,406, filed on Oct. 7, 2002, provisional application No. 60/416,407, filed on Oct. 7, 2002, provisional application No. 60/416,408, filed on Oct. 7, 2002, provisional application No. 60/416,409, filed on Oct. 7, 2002.

(51) Int. Cl.
*A61B 5/02* (2006.01)
*A61B 5/04* (2006.01)
*A61N 1/00* (2006.01)

(52) U.S. Cl. ............... 600/508; 600/481; 600/483; 600/485; 600/486; 607/60; 607/126

(58) Field of Classification Search ......... 600/481, 600/483, 485, 486, 508, 513, 322; 607/60, 607/126; 128/903
See application file for complete search history.

(56) References Cited

U.S. PATENT DOCUMENTS

| | | | |
|---|---|---|---|
| 5,135,538 A * | 8/1992 | Pawlak et al. ............. 623/2.25 |
| 5,368,040 A | 11/1994 | Carney | |
| 5,476,484 A * | 12/1995 | Hedberg ..................... 607/23 |
| 6,053,873 A * | 4/2000 | Govari et al. ............... 600/505 |
| 6,092,530 A * | 7/2000 | Weissman et al. .......... 128/899 |
| 6,111,520 A | 8/2000 | Allen | |
| 6,277,078 B1 | 8/2001 | Porat | |
| 6,278,379 B1 | 8/2001 | Allen | |
| 6,328,699 B1 | 12/2001 | Eigler | |
| 6,409,674 B1 | 6/2002 | Brockway | |
| 6,432,050 B1 | 8/2002 | Porat | |
| 6,475,170 B1 | 11/2002 | Doron | |
| 6,486,588 B2 | 11/2002 | Doron | |
| 6,636,769 B2 * | 10/2003 | Govari et al. ................. 607/60 |

* cited by examiner

Primary Examiner—Robert E. Pezzuto
Assistant Examiner—Natasha Patel
(74) Attorney, Agent, or Firm—Gary M. Hartman; Domenica N. S. Hartman; Hartman & Hartman, P.C.

(57) ABSTRACT

A system for non-invasively monitoring one or more physiological parameters such as pressure and/or pressure gradients in a cardiac conduit adapted for blood bypass flow. The system includes the conduit, at least one sensing device chronically located within the conduit, and a non-implantable readout device. The sensing device includes at least one inductor coil and at least one sensor for monitoring the one or more physiological parameters for diagnosis of the condition of the conduit after the conduit is implanted in a patient. The readout device includes at least one inductor coil allowing electromagnetic telecommunication and electromagnetic wireless powering of the sensing device through the inductor coil thereof.

32 Claims, 2 Drawing Sheets

SYSTEM FOR MONITORING CONDUIT OBSTRUCTION

REFERENCE TO PREVIOUS APPLICATIONS

This application claims the benefit of U.S. Provisional Applications No. 60/416,406 filed on Oct. 7, 2002, 60/416,407 filed on Oct. 7, 2002, 60/416,408 filed on Oct. 7, 2002, and 60/416,409 filed on Oct. 7, 2002.

FIELD OF THE INVENTION

The present invention relates generally to field of implantable medical devices for monitoring physiological parameters. More particularly, the invention relates to a system utilizing a telemetric implantable physiologic sensor for diagnosing and/or monitoring the conduit obstruction and/or insufficiency in patients that have undergone cardiac conduit surgery.

BACKGROUND OF THE INVENTION

Certain heart defects require implantation of a conduit for blood flow to bypass valve aplasia or severe stenosis. These include but not limited to cases of a pulmonary artery only with no aorta. The added conduit may or may not include a valve. There are several types of conduits, including but not limited to:

Homograft—from the same species (i.e. another human)
Heterograft—from a different species (e.g. pig)
Artificial—man-made materials (e.g. Gortex)
Combination of two or more of the above.

In any case, the conduits may eventually become calcified and/or stenotic. Currently, cardiac catheterization, Doppler echocardiography, and/or Magnetic Resonance Imaging (MRI) are used to assess the degree of stenosis. Catheterization gives the best assessment, since it can directly measure the pressure gradient across the conduit; however, it carries progressive morbidity and mortality. Furthermore, all three methods require specialized equipment and they provide only a snapshot of the physiologic status.

Occlusion is an eventuality in nearly all conduit cases; the question is only a matter of when it will occur. The impact of occlusion includes right ventricle (RV) failure. Treatment for occlusion is to replace the conduit entirely. Physicians need a means of noninvasively, accurately monitoring conduit condition on a continuous basis in order to determine whether and when conduit revision is required. Furthermore, remote monitoring of conduit condition would simultaneously reduce the number of hospital and clinic visits while increasing the overall timeliness of treatment.

SUMMARY OF THE INVENTION

The invention comprises a telemetric sensing system for noninvasively monitoring pressure and/or pressure gradients in a cardiac conduit. The system includes one or more implantable sensor unit(s) and a companion reader unit. The sensor unit, which is preferably batteryless and wireless is chronically located within the conduit, or around in a close proximity. For valveless conduits, a sensor unit is placed at either end of the conduit, or around it. For valved conduits, one or more sensor units are located both proximal and distal to the valve, allowing the pressure gradient across the valve to be monitored. One sensor unit can indicate occlusion; however, two sensor units will allow the occlusion to be located (e.g. proximal/middle/distal along the conduit). As well, with two sensor units, flow rates may be deduced or estimated. Furthermore, trend analysis of the pressures and/or flow rate within the conduit can allow a time-to-failure estimate.

DETAILED DESCRIPTION OF PREFERRED AND ALTERNATE EMBODIMENTS OF THE INVENTION

The following description of preferred embodiments and methods provides examples of the present invention. The embodiments discussed herein are merely exemplary in nature, and are not intended to limit the scope of the invention in any manner. Rather, the description of these preferred embodiments and methods serves to enable a person of ordinary skill in the relevant art to make, use and perform the present invention.

Figure 1:
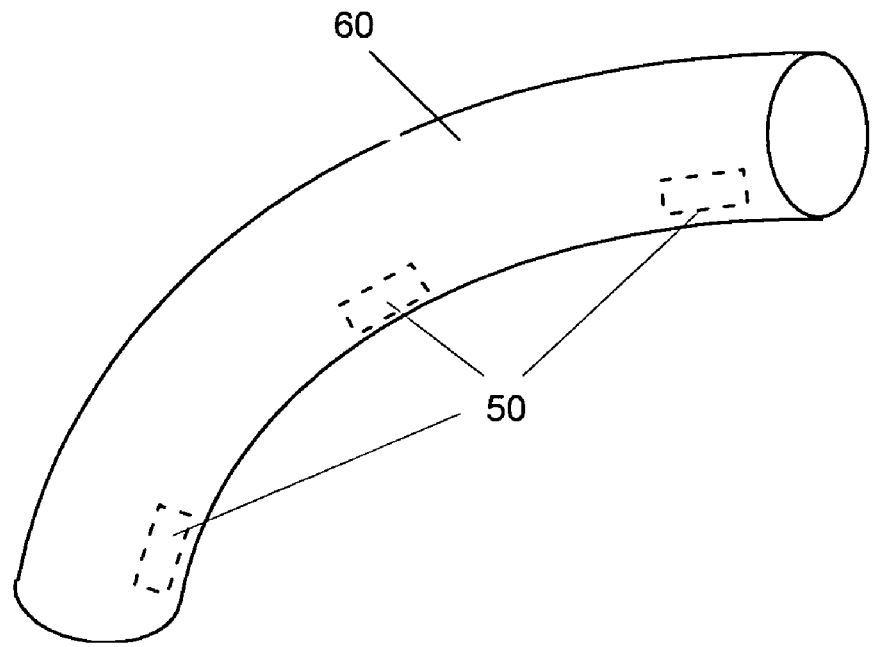
FIG. 1 is a schematic of an implantable pressure monitor fixed in a cardiac conduit.

In order to provide for the effective monitoring, management, and tailoring of treatment for patients with heart defects, the present invention provides a cardiac conduit with a wireless sensing system. The system comprises an external readout unit as well as at least one implantable sensor 50 which is securely anchored in a conduit 60, as shown in FIG. 1 or in the vicinity of the conduit. The readout unit both transmits power to and receives transmitted data from the sensor 50. Data transmitted from the sensor 50 may include pressure, calibration data, identification data, fluid flow rate, and/or other physiologic parameters. The readout unit may include a barometric pressure sensor in order to compensate for variation in atmospheric pressure.

As noted above, at least one sensor 50 is chronically located within the conduit 60, or around it. For valveless conduits 60, one or more sensors 50 are placed at either end of the conduit 60. For valved conduits 60, a sensor 50 is located both proximal and distal to the valve, allowing the pressure gradient across the valve to be monitored. One sensor 50 can indicate occlusion; however, two sensors 50 will allow the occlusion to be located (e.g. proximal/middle/distal along the conduit 60). As well, with two sensors 50, flow rates may be deduced or estimated. Furthermore, trend analysis of the pressures and/or flow rate within the conduit 60 can allow a time-to-failure estimate.

Figure 2:
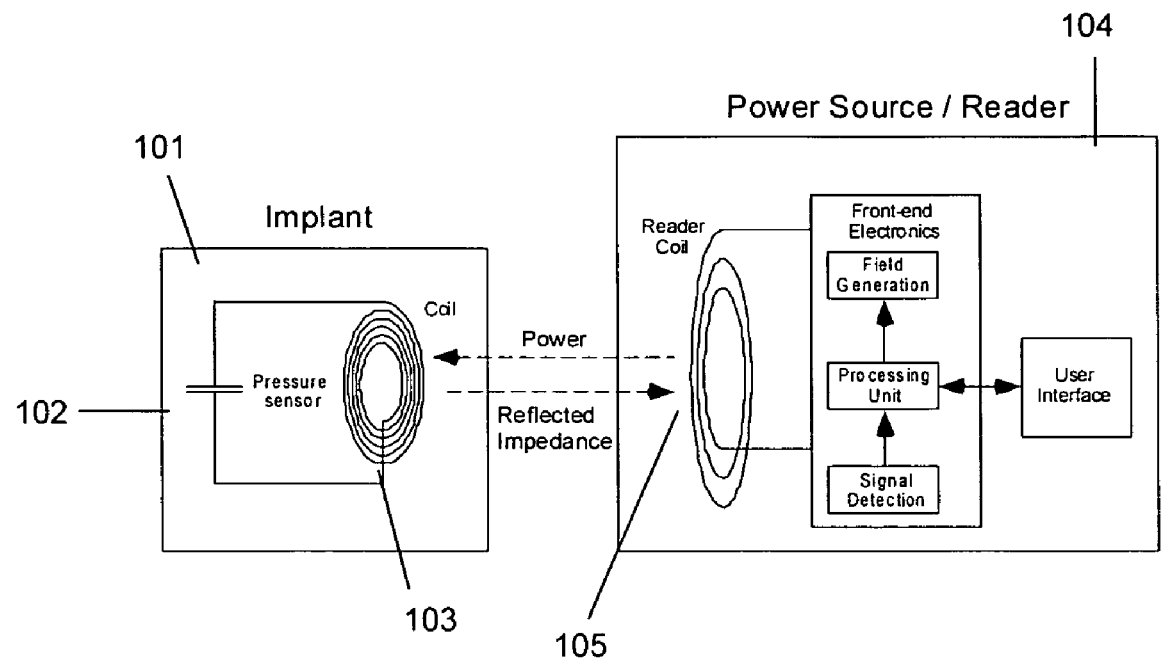
FIG. 2 is a block diagram of a magnetic telemetry based physiologic monitoring system based on a resonant scheme according to a preferred embodiment of the present invention.

The batteryless, wireless telemetry link between the sensor(s) 50 and the reader unit is preferably implemented using either a resonant or passive, magnetically coupled scheme. A resonant device 101 (shown in FIG. 2) is the simplest approach, and consists only of a packaged inductor coil 103 and capacitive pressure sensor 102. Together, the sensor 102 and coil 103 form a circuit that has a specific resonant frequency. At that resonant frequency, the circuit presents a measurable change in magnetically coupled impedance load to an external coil 105 associated with an external reader 104. Because the resonant frequency is a function of the inductance of the coil 103 and the sensor capacitance of the sensor 102, as pressure changes the resonant frequency changes as well. The external reader 104 is able to determine pressure by monitoring the frequency at which the coil antenna 105 impedance changes.

Figure 3:
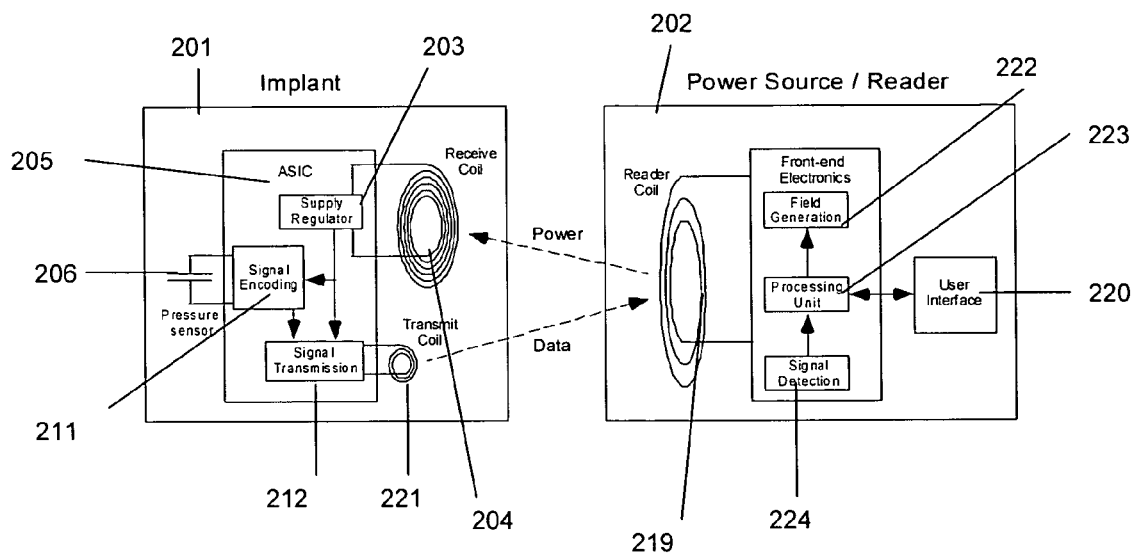
FIG. 3 is a block diagram of a magnetic telemetry based physiologic monitoring system based on a passive scheme according to an alternate embodiment of the present invention.

The preferred communication scheme for the present invention, shown in FIG. 3 as being between a passive implant device 201 and an external reader 202, is based on magnetic telemetry. Devices that have on-board circuitry but still receive their operating power from an external source (i.e., are batteryless) are referred to herein as passive. Without the external reader 202 present, the implant device 201 lays passive and without any internal means to power itself. When a pressure reading is desired, the reader 202 is brought into a suitable range to the implant device 201. In this case the external reader 202 uses an alternating magnetic field to induce a voltage in the implant device 201. When sufficient voltage has been induced in the implant device 201, a rectification circuit 203 converts the alternating voltage on the receiver coil 204 into a direct voltage that can be used by the electronics 205 as a power supply for signal conversion and communication. At this point the implant device 201 can be considered alert and, in the preferred embodiment, also ready for commands from the reader 202. The maximum achievable distance is mostly limited by the magnetic field strength necessary to turn the implant device 201 on. This telemetry scheme has been proven and used extensively in the identification and tracking industry (e.g., implantable RF ID technology from Texas Instruments or Digital Angel) with a great deal of acceptance and success.

Once the direct voltage in the implant device 201 has been established for the circuit operation, a number of techniques may be used to convert the output of the device 201 into a form suitable for transmission back to the reader 202. In the preferred embodiment, a capacitive pressure sensor 206 and sigma delta conversion or capacitance to frequency conversion of the sensor output may be easily used. Capacitive sensors are preferred due to the small power requirements for electronics when reading capacitance values. Many pressure sensors are based on piezoresistive effects and, while suitable for some applications, do suffer in this application due to the higher power levels needed for readout. Sigma delta converters are preferred due to the tolerance of noisy supply voltages and manufacturing variations.

As those skilled in magnetic telemetry are aware, a number of modulation schemes are available for transmitting data via magnetic coupling. The preferred schemes include but are not limited to amplitude modulation, frequency modulation, frequency shift keying, phase shift keying, and also spread spectrum techniques. The preferred modulation scheme may be determined by the specifications of an individual application, and is not intended to be limited under this invention.

In addition to the many available modulation techniques, there are many technologies developed that allow the implant device 201 to communicate back to the reader 202 the signal containing pressure information. It is understood that the reader 202 may transmit either a continuous level of RF power to supply the needed energy for the device 201, or it may pulse the power allowing temporary storage in a battery or capacitor device (not shown) within the device 201. Similarly, the implant device 201 of FIG. 3 may signal back to the reader 202 at any interval in time, delayed or instantaneous, during reader RF (Radio Frequency) transmission or alternately in the absence of reader transmission. The implant device 201 may include a single coil antenna 204 for both reception and transmission, or it may include two antennas 204 and 221, one each for transmission 204 and reception, respectively. There are many techniques for construction of the reader coil 219 and processing electronics known to those skilled in the art. The reader 202 may interface to a display, computer, or other data logging devices 220.

The electronic circuit may consist of the coil antenna 204, rectification circuitry 203, signal conditioning circuitry 211, and signal transmission circuitry 212.

A large number of possible geometries and structures are available for the coil 204 and are known to those skilled in the art. The coil conductor may be wound around a ferrite core to enhance magnetic properties, deposited on a flat rigid or flexible substrate, and formed into a long/skinny or short/wide cylindrical solenoid. The conductor is preferably made at least in part with a metal of high conductivity such as copper, silver, or gold. The coil 204 may alternately be fabricated on implantable sensor substrates. Methods of fabrication of coils on the sensor substrate include but are not limited to one or more or any combination of the following techniques: sputtering, electroplating, lift-off, screen printing, and/or other suitable methods known to those skilled in the art.

The rectification circuitry 203 outputs a constant voltage level for the other electronics from an alternating voltage input. Efficient realizations of such circuitry are standard electronic techniques and may include either full bridge diode rectifiers or half-bridge diode rectifiers in the preferred embodiment. This rectification circuitry may include a capacitor for transient energy storage to reduce the noise ripple on the output supply voltage. This circuitry may be implemented on the same integrated circuit die with other electronics.

The signal conditioning circuit 211 processes an output signal from the sensor 206 and prepares it for transmission to an external receiving and/or analyzing device. For example, many pressure sensors output a capacitance signal that may be digitized for radio frequency (RF) transmission. Accordingly, the signal conditioning circuit 211 places the output signal of the sensor into an appropriate form. Many different signal conditioning circuits are known to those skilled in the art. Capacitance to frequency conversion, sigma delta or other analog to digital conversion techniques are all possible conditioning circuits that may be used in a preferred embodiment.

The signal transmission circuitry 212 transmits the encoded signal from the signal conditioning circuitry 211 for reception by the external reader 202. Magnetic telemetry is again used for this communication, as the transmission circuitry 212 generates an alternating electromagnetic field that propagates to the reader 202. Either the same coil 204 is used for signal reception and for transmission, or alternately the second coil 221 is dedicated for transmission only.

A third option, particularly useful for (but not limited to) situations in which long-term data acquisition without continuous use of the readout unit is desirable, is to implement the sensor using an active scheme. This approach incorporates an additional capacitor, battery, rechargeable battery, or other power-storage element that allows the implant to function without requiring the immediate presence of the readout unit as a power supply. Data may be stored in the sensor and downloaded intermittently using the readout unit as required.

The implantable sensor may be physically realized with a combination of any of several technologies, including those using microfabrication technology such as Microelectromechanical Systems (MEMS). For example, capacitive and piezoresistive pressure sensors have been fabricated with MEMS technology. A hermetic sensor package may be formed from anodically bonded layers of glass and boron-doped silicon, which is further incorporated into the Fontan baffle structure.

Anchoring provisions may be incorporated directly into such a hermetic package, or they may alternately be added with an additional assembly step. An example of this would be insertion of the package into a molded plastic or metal shell that incorporates anchoring provisions. Possible anchoring methods include those conventionally used for cardiac pacing leads, such as screws or tines, as well as septal occluder schemes. Many such packaging schemes are known to those familiar with the art, and the present description should not be construed as limiting.

Figure 4:
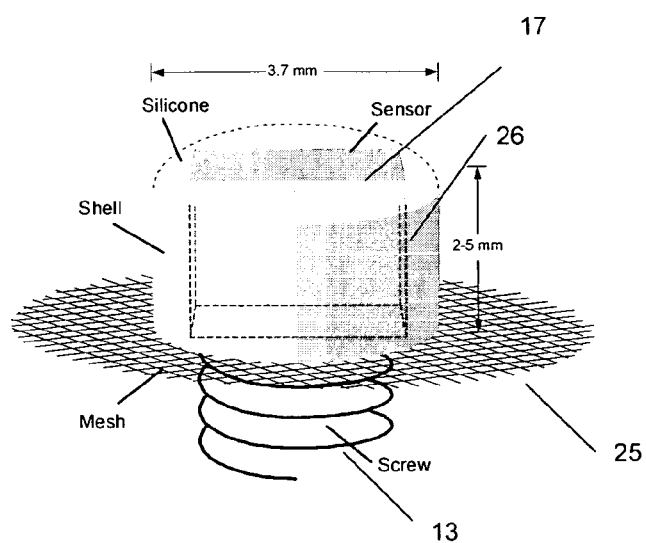
FIG. 4 is a perspective view of a sensor implant incorporating a screw anchoring mechanism according to a preferred embodiment of the present invention.

Pacemaker leads have a well-established history for implantation methods, and similar techniques are possible for the current invention. A screw 13 (FIG. 4) or barb may be used to attach the implant to a heart or vessel wall. In the first package option shown in FIG. 4, a screw 13 may be molded into the device shell 26, and screwed into the ventricle wall so that that the screw buries below the wall surface. In addition, the package may have mesh 25 attached to the device to promote tissue growth and anchoring.

In addition to the basic implant-and-reader system, a number of other embodiments of the technology can be realized to achieve additional functionality. The system may be implemented as a remote monitoring configuration, including but not limited to home monitoring, which may include but not limited to telephone based, wireless communication based, or web-based (or other communication means) delivery of information received from the implant by the reader to a physician or caregiver.

The implantable sensor can be any suitable miniature sensor adapted to detect and/or monitor various physiological parameters. For example, the sensor can comprise a pressure sensor, a temperature sensor, a flow sensor, a velocity sensor, or a sensor adapted to measure specific chemistries such as gas content (e.g., $O_2$ and $CO_2$) and glucose levels. Various specific examples of these types of miniature sensors are known to those skilled in the art, and any one or more of these suitable sensors can be utilized in the sensor module of the present invention. While the specific type of sensor(s) chosen will depend on the application of the implantable system, the sensor(s) should be of a sufficiently small size in order to facilitate placement within a catheter for delivery and implantation.

To limit the risk of thrombogenesis, the preferred embodiment has limited protrusion of volume into the blood stream (particularly in the left side of the heart), as both shape and size are factors in thrombogenesis. Another shell may be overmolded or preformed to house the glass/silicon module, and the outer shell contains the necessary apparatus for anchoring the implant. In a preferred embodiment, the outer shell may be formed with existing plastic injection technologies suitable for medical implantation. A coating, preferably of silicone, parylene and/or polymers provides a non-thrombogenic exterior for the biologic environment.

Note that in addition to sensing physiologic parameters, the described system could be augmented with various actuation functions. In such case, the implant device would be augmented with any of various actuators, including but not limited to: thermal generators; voltage or current sources, probes, or electrodes; drug delivery pumps, valves, or meters; microtools for localized surgical procedures; radiation-emitting sources; defibrillators; muscle stimulators; pacing stimulators.

Finally, the cardiac conduit 60 with the attached sensor 50 and remote readout device can be implemented as part of a closed-loop medical treatment system. Furthermore, if the conduit 60 includes a valve, the cardiac conduit can be incorporated into a closed-loop or open-loop system for control of the valve.

The foregoing disclosure includes the best mode devised by the inventors for practicing the invention. It is apparent, however, that several variations in the apparatuses and methods of the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations.

We claim:

1. A cardiac conduit system comprising:
   an implantable cardiac conduit adapted for carrying blood flow to bypass a conduit of a patient's heart when implanted in the patient, wherein said cardiac conduit is adapted for carrying blood flow to bypass valve aplasia or severe stenosis of the patient's heart and said cardiac conduit includes a valve;
   at least one sensing device chronically located within said cardiac conduit, said sensing device comprising of at least one inductor coil and at least one means for monitoring one or more physiological parameters for diagnosis of the condition of said cardiac conduit after said cardiac conduit is implanted in the patient, with optional electronic components; and
   a non-implantable readout device comprising at least one inductor coil allowing electromagnetic telecommunication and electromagnetic wireless powering of said sensing device through said at least one inductor coil of said sensing device.

2. The cardiac conduit system of claim 1 wherein said at least one sensing device comprises of at least one capacitive sensor.

3. The cardiac conduit system of claim 1 wherein said at least one sensing device includes a battery.

4. The cardiac conduit system of claim 3 wherein said battery is rechargeable using wireless means.

5. The cardiac conduit system of claim 1 wherein said physiological parameters include pressure.

6. The cardiac conduit system of claim 1 wherein said physiological parameters include pressure gradient.

7. The cardiac conduit system of claim 1 wherein said cardiac conduit is adapted to be implanted in the patient so that after said cardiac conduit is implanted in the patient said at least one sensing device measures at least one of the following pressures: pulmonary artery, left atrium, right atrium, left atrium appendage, right atrium appendage, mean left atrium pressure, mean right atrium pressure, differential pressure between left and right atrium.

8. The cardiac conduit system of claim 7 further comprising means for calculating change of pressure over time, dp/dt.

9. The cardiac conduit system of claim 1 wherein said cardiac conduit is chosen from the group consisting of homograft, heterograft, and artificial conduits.

10. The cardiac conduit system of claim 1 wherein said at least one sensing device is located at one end of said cardiac conduit.

11. The cardiac conduit system of claim 10 wherein said at least one sensing device comprises a second sensing device at a second end of said cardiac conduit.

12. The cardiac conduit system of claim 1 wherein said at least one sensing device is adapted to indicate occlusion of said cardiac conduit.

13. The cardiac conduit system of claim 12 wherein said at least one sensing device comprises a second sensing device and said sensing devices are located on said cardiac conduit so as to be operable for locating the occlusion.

14. The cardiac conduit system of claim 1 wherein said at least one sensing device comprises a second sensing device and said sensing devices are adapted for measuring flow rates through said cardiac conduit.

15. The cardiac conduit system of claim 1 wherein data from said at least one sensing device are useful to estimate time-to-failure within said cardiac conduit.

16. The cardiac conduit system of claim 1 wherein said at least one sensing device and said readout device are adapted for use for one or more of the following diagnosis: assessment of stenosis, assessment of occlusion assessment of inefficiency of said cardiac conduit.

17. The cardiac conduit system of claim 1 wherein one or more of the following schemes are used to couple said at least one sensing device to said readout device: resonant, passive, active.

18. The cardiac conduit system of claim 1 wherein said one or more physiological parameters are one or more of the following parameters: pressure, temperature, flow, blood composition, blood gas content, chemical composition, chemical concentration, acceleration, vibration.

19. The cardiac conduit system of claim 1 wherein said at least one sensing device and said readout device are adapted for use for one or more of the following applications: early diagnosis of stenosis in said cardiac conduit, early diagnosis of occlusion in said cardiac conduit, early diagnosis inefficiency of said cardiac conduit, early diagnosis of congenital heart diseases, congestive heart failure, and related conditions, early intervention in treatment of congenital heart diseases, congestive heart failure. and related conditions, remote monitoring of patients with congenital heart diseases, congestive heart failure, and related conditions, tailoring of medications, heart disease management, identification of complications from the condition of said cardiac conduit in patients with congenital heart diseases, congestive heart failure, and related conditions, identification of complications from the condition of said cardiac conduit in patients with congenital heart diseases, congestive heart failure, and related conditions, treatment of complications from the condition of said cardiac conduit in patients with congenital heart diseases, congestive heart failure, and related conditions, treatment of complications from the condition of said cardiac conduit in patients with congenital heart diseases, congestive heart failure, and related conditions, feedback regarding the impact of medication on the heart, reduction in frequency and severity of hospitalizations due to congenital heart diseases and congestive heart failure, reduction in frequency and severity of hospitalizations due to congenital heart diseases and congestive heart failure, identification of mitral valve stenosis, and treatment of mitral valve stenosis including surgery and balloon angioplasty.

20. The cardiac conduit system of claim 1 wherein said readout device is capable of performing one or more of the following: remote monitoring of said cardiac conduit in heart disease patients, including home monitoring, monitoring of said cardiac conduit in heart disease patients with telephone-based (or similar method) data and information delivery, monitoring of said cardiac conduit in heart disease patients with wireless telephone-based (or similar method) data and information delivery, monitoring of said cardiac conduit in heart disease patients with web-based (or similar method) data and information delivery, closed-loop drug delivery to treat heart disease, closed-loop tuning of medical systems to treat heart disease, congestive heart failure, or congenital heart disease related conditions, warning systems for critical worsening of said cardiac conduit in heart disease patients, portable or ambulatory monitoring or diagnostic systems, battery-operation capability, data storage, reporting global positioning coordinates for emergency applications, communication with other medical devices including pacemakers, defibrillator, implantable cardioverter defibrillator, implantable drug delivery systems, non-implantable drug delivery systems, and wireless medical management systems.

21. The cardiac conduit system of claim 1 wherein said at least one sensing device comprises means for anchoring said at least one sensing device to said cardiac conduit.

22. The cardiac conduit system of claim 21, wherein said anchoring means comprises at least one anchoring mechanism used in one or more of the following: septal occluder devices, left atrial appendage occluders, cardiac pacing leads, screws, tines, stents.

23. The cardiac conduit system of claim 21 wherein said anchoring means is a part of said cardiac conduit.

24. The cardiac conduit system of claim 21 wherein said anchoring means is a helical screw.

25. The cardiac conduit system of claim 21 wherein said anchoring means is a tine.

26. The cardiac conduit system of claim 21 wherein said anchoring means is made from one or more materials chosen from the group consisting of nitinol, teflon, stainless steel, polymer, titanium, and biocompatible metals.

27. The cardiac conduit system of claim 1 wherein said at least one sensing device is augmented with one or more actuators chosen from the group consisting of thermal generators, voltage sources, current sources, probes, electrodes, drug delivery pumps, valves, meters, microtools for localized surgical procedures, radiation emitting sources, defibrillators, muscle stimulators, and pacing stimulators.

28. The cardiac conduit system of claim 1 wherein said cardiac conduit system is part of a closed-loop medical treatment system.

29. The cardiac conduit system of claim 1 wherein at least a portion of said at least one sensing device is coated with one or more layers of thin coatings.

30. The cardiac conduit system of claim 29 wherein the one or more layers of thin coatings are formed of one or more coating materials chosen from the group consisting of silicone, hydrogels, parylene, polymer, nitrides, oxides, nitric-oxide generating materials, carbides, silicides, and titanium.

31. The cardiac conduit system of claim 1 wherein said cardiac conduit system is incorporated into a closed-loop system for control of said valve in said cardiac conduit.

32. The cardiac conduit system of claim 1 wherein said cardiac conduit system is incorporated into an open-loop system for control of said valve in said cardiac conduit.

* * * * *